US012227734B2

(12) United States Patent
Rao et al.

(10) Patent No.: US 12,227,734 B2
(45) Date of Patent: Feb. 18, 2025

(54) MICROSCALE BIOPROCESSING SYSTEM AND METHOD FOR PROTEIN MANUFACTURING FROM HUMAN BLOOD

(71) Applicant: University of Maryland, Baltimore County, Baltimore, MD (US)

(72) Inventors: Govind Rao, Ellicott City, MD (US); Yordan Kostov, Columbia, MD (US); Leah Tolosa Croucher, Columbia, MD (US); Kevin Tran, Marriotsville, MD (US); Monohar Pilli, Gwynn Oak, MD (US); Michael Tolosa, Columbia, MD (US); Chandrasekhar Gurramkonda, Halethorpe, MD (US); David Burgenson, Daly City, CA (US)

(73) Assignee: University of Maryland, Baltimore County, Baltimore, MD (US)

( * ) Notice: Subject to any disclaimer, the term of this patent is extended or adjusted under 35 U.S.C. 154(b) by 36 days.

(21) Appl. No.: 17/837,772

(22) Filed: Jun. 10, 2022

(65) Prior Publication Data
US 2022/0298469 A1 Sep. 22, 2022

Related U.S. Application Data

(63) Continuation of application No. 15/329,555, filed as application No. PCT/US2015/043314 on Jul. 31, 2015, now abandoned.

(60) Provisional application No. 62/031,484, filed on Jul. 31, 2014.

(51) Int. Cl.
C07K 9/00 (2006.01)
A61K 35/14 (2015.01)
A61M 1/36 (2006.01)
B01D 15/08 (2006.01)
B01D 15/32 (2006.01)
B01D 15/36 (2006.01)
B01D 15/38 (2006.01)
C07K 1/36 (2006.01)
C12M 1/00 (2006.01)
C12M 1/40 (2006.01)

(52) U.S. Cl.
CPC ............ *C12M 47/12* (2013.01); *A61K 35/14* (2013.01); *A61M 1/3621* (2013.01); *B01D 15/08* (2013.01); *B01D 15/327* (2013.01); *B01D 15/361* (2013.01); *B01D 15/3847* (2013.01); *C07K 1/36* (2013.01); *C12M 21/18* (2013.01); *C12M 29/04* (2013.01)

(58) Field of Classification Search
CPC ...... C12M 47/12; C12M 21/18; C12M 29/04; B01D 15/327; B01D 15/361; B01D 15/3847; C07K 1/36; A61M 1/0259
See application file for complete search history.

(56) References Cited

U.S. PATENT DOCUMENTS

| 4,156,681 | A | 5/1979 | Schneider et al. |
| 4,303,193 | A | 12/1981 | Latham, Jr. |
| 5,112,949 | A | 5/1992 | Vukovich |
| 5,785,869 | A | 7/1998 | Martinson et al. |
| 5,968,767 | A | 10/1999 | Sheikh et al. |
| 6,642,024 | B1 | 11/2003 | Pennica |
| 6,670,173 | B1 | 12/2003 | Schels et al. |
| 6,673,532 | B2 | 1/2004 | Rao |
| 6,905,843 | B1 | 6/2005 | Endo et al. |
| 6,946,075 | B2 | 9/2005 | Kopf |
| 7,041,493 | B2 | 5/2006 | Rao |
| 7,485,454 | B1 | 2/2009 | Jury et al. |
| 9,163,272 | B2 | 10/2015 | Park et al. |
| 9,388,373 | B2 | 7/2016 | Rao |
| 9,982,227 | B2 | 5/2018 | Rao et al. |
| 10,435,664 | B2 | 10/2019 | Rao |
| 2008/0248521 | A1 | 10/2008 | Knapp et al. |
| 2008/0269468 | A1 | 10/2008 | Vogel et al. |
| 2008/0287656 | A1 | 11/2008 | Peters et al. |
| 2009/0178495 | A1 | 7/2009 | Steigmiller et al. |
| 2010/0298172 | A1 | 11/2010 | Desmond et al. |
| 2011/0065084 | A1 | 3/2011 | Rao et al. |
| 2012/0024788 | A1 | 2/2012 | Kelso et al. |
| 2013/0280797 | A1 | 10/2013 | Rao et al. |

FOREIGN PATENT DOCUMENTS

| EP | 1775000 | 4/2007 |
| EP | 2302407 | 3/2011 |
| WO | WO 2005/063808 | 7/2005 |
| WO | WO 2008/066583 | 6/2008 |
| WO | WO 2016/019350 | 2/2016 |

OTHER PUBLICATIONS

Waters et al. (2013). A Practical and Novel Method to Extract Genomic DNA from Blood Collection Kits for Plasma Protein Preservation. Journal of Visualized Experiments. p. 1-6.*
Bank et al., Protein synthesis in a cell free human reticulocyte system: ribosome function in thalassemia. J Clin Invest. Mar. 1966;45(3):330-6.
Calhoun et al., Energy Systems for ATP Regeneration in Cell-Free Protein Synthesis Reactions, in: In Vitro Transcription and Translation Protocols, 2nd edition, Guido Grandi ed., 2007 Humana Press Inc., New Jersey. 23 pages.
Extended European Search Report issued in EP application No. 15827147.8 on Feb. 20, 2018.
Office Action issued in Canadian patent application No. 2956924, Oct. 30, 2018. 4 pp.

(Continued)

*Primary Examiner* — Jeanette M Lieb
(74) *Attorney, Agent, or Firm* — Casimir Jones, SC; Tristan A. Fuierer

(57) ABSTRACT

A bioprocessing system for protein manufacturing from human blood is provided that is compact, integrated and suited for on-demand production and delivery of therapeutic proteins to patients. The parent's own blood can be used as the source of cell extracts for the production of the therapeutic proteins.

19 Claims, 11 Drawing Sheets

(56) References Cited

OTHER PUBLICATIONS

Office Action, U.S. Appl. No. 16/660,993; Dated Apr. 15, 2020. 13 pages.
Pierce. Protein stability and Storage, Technical resource, 2005, updated Jul. 14, 2015. pp. 1-3.
Salehi et al., Cell-free protein synthesis of a cytotoxic cancer therapeutic: Onconase production and a just-add-water cell-free system. Biotechnol J. Feb. 2016;11(2). 24 pages.
Sun et al., Protein degradation in a TX-TL cell-free expression system using ClpXP protease. TechnicalReport, Jul. 8, 2014, http://www.cds.caltech.edu/~murray/papers/sksm14-clpxp.html . 11 pages.

* cited by examiner

MICROSCALE BIOPROCESSING SYSTEM AND METHOD FOR PROTEIN MANUFACTURING FROM HUMAN BLOOD

This application is continuation of co-pending U.S. patent application Ser. No. 15/329,555, filed on Jan. 26, 2017, which was filed under 35 U.S.C. § 371 and claims priority to International Patent Application No. PCT/US2015/043314, filed on Jul. 31, 2015, which claims priority to U.S. Provisional Patent Application No. 62/031,484, filed on Jul. 31, 2014, all of which are incorporated by reference herein in their entireties.

BACKGROUND OF THE INVENTION

1. Field of the Invention

The present invention relates to protein manufacturing and, more particularly, to an integrated and compact bioprocessing system for the production or manufacturing of therapeutic proteins using human blood.

2. Background of the Related Art

The time it takes for a new drug to reach the market is 8-10 years at a cost approaching $1.2 billion. Many of these new drug entities are referred to as biologics (e.g., a protein used as a drug or therapeutic). These are molecules produced by living cells in vitro using cell culture and fermentation technologies. Stringent process control is required since changes in culture conditions can lead to, for example, altered glycosylation profiles, which can then drastically change the drug's pharmacokinetics, efficacy and immunogenicity. Therefore, much effort towards FDA approval is devoted to the development of documented and robust manufacturing processes that will produce safe and efficacious biologics of consistent quality. These are collectively referred to as good manufacturing processes (GMP). The goal is to arrive at a process that is well defined and reproducible, and that leads to products that meet predetermined characteristics of quality, identity, purity, safety and efficacy.

Currently, companies are developing 907 biologics that are targeting over 100 diseases. All these biologics share one thing in common-they are produced in a centralized manufacturing facility with large scale (>10,000 liters) living cell cultures, and with the necessary large volume separation, purification, formulation, packaging, and distribution infrastructure (e.g. a typical MERCK®, PFIZER® or GENENTECH® plant). The time period from a cell bank to the final delivery of the therapeutic vial is on the order of 6-8 weeks under ideal conditions and produces batches of around 10 Kg bulk protein.

As shown in FIGS. 1A and 1B, the process itself is complex. Figure LA is a schematic diagram of a typical manufacturing paradigm used by a typical biologic manufacturing facility. A manufacturing facility such as this is typically found at any large pharmaceutical/biotechnology company and is currently the only means of making therapeutic proteins. Such a manufacturing facility costs several hundred million dollars to build and takes approximately two years to commission.

FIG. 1B shows a typical flow sheet for the manufacturing of protein biologics—both for proteins that are expressed intracellularly and proteins expressed extracellularly. Every step needs to be individually developed, scaled-up, optimized and validated in a manufacturing setting. The final product will also have an expiration date and is either shipped lyophilized or via a cold chain, which must also be documented. It is easy to see why making a therapeutic protein is a non-trivial task and getting from the bench to the clinic is a long process. The situation is worse if the disease is a rare one for which drugs are available, but are simply not profitable. These types of drugs are designated as "orphan drugs" and carry incentives so that the private sector will produce them.

Accordingly, there is a critical need for technology that can rapidly produce neutralizing antibodies for infectious diseases. The current system for producing such neutralizing antibodies requires several months, which is untenable, as the recent outbreaks of H1N1, SARS and Ebola have illustrated. In addition, the current approach is unsuitable for personalized therapeutics.

SUMMARY OF THE INVENTION

An object of the invention is to solve at least the above problems and/or disadvantages and to provide at least the advantages described hereinafter.

Therefore, an object of the present invention is to provide an integrated and compact bioprocessing system for the production of proteins.

Another object of the present invention is to provide an integrated and compact bioprocessing system for the production of proteins from human blood.

Another object of the present invention is to provide an integrated and portable bioprocessing system for the production of proteins.

Another object of the present invention is to provide an integrated and portable bioprocessing system for the production of proteins from human blood.

Another object of the present invention is to provide an integrated and compact bioprocessing system for protein expression and purification.

Another object of the present invention is to provide an integrated and compact bioprocessing system for protein expression and purification from human blood.

Another object of the present invention is to provide a method for on-demand production and delivery of a therapeutic protein to a patient.

Another object of the present invention is to provide a method for on-demand production of a therapeutic protein from human blood and delivery of the therapeutic protein to a patient.

Another object of the present invention is to provide a method for on-demand production of a therapeutic protein from a patient's blood and delivery of the therapeutic protein to the patient.

To achieve at least the above objects, in whole or in part, there is provided a bioprocessing system, comprising a production module for producing a protein from cells extracted from blood and a purification module for receiving the protein from the production module and for purifying the protein from reagents.

To achieve at least the above objects, in whole or in part, there is also provided a system for delivering a therapeutic protein to a patient, comprising a cell extraction module for extracting cells from blood obtained from the patient, a reactor for therapeutic protein expression using the cells extracted from the patient's blood and a purification module for receiving the protein from the production module and for purifying the protein from reagents.

Additional advantages, objects, and features of the invention will be set forth in part in the description which follows and in part will become apparent to those having ordinary skill in the art upon examination of the following or may be learned from practice of the invention. The objects and advantages of the invention may be realized and attained as particularly pointed out in the appended claims.

BRIEF DESCRIPTION OF THE DRAWINGS

The invention will be described in detail with reference to the following drawings in which like reference numerals refer to like elements wherein.

DETAILED DESCRIPTION OF PREFERRED EMBODIMENTS

The present invention is particularly suited for the on-demand manufacturing of therapeutic proteins (either cell-based or cell-free) that are suitable for direct delivery to a patient. Therefore, the present invention will be primarily described and illustrated in connection with the manufacturing of therapeutic proteins. However, the present invention can also be used to manufacture any type of protein. Further, the present invention is particularly suited for the on-demand manufacturing of proteins using cell-free expression, and thus the present invention will be described primarily in the context of cell-free protein expression. However, the present invention can also be used in connection with cell-based protein expression.

Figure 1A:
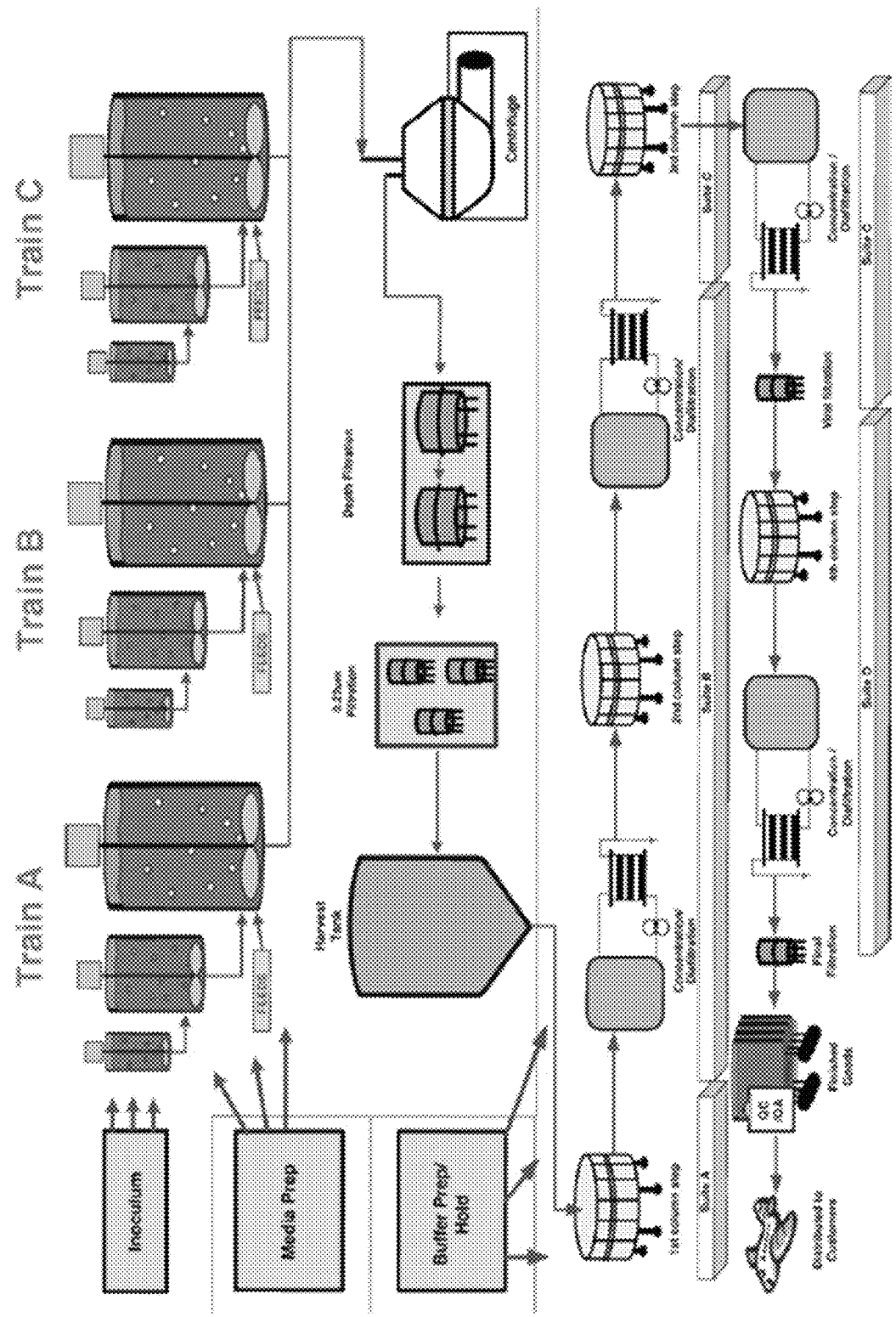
FIG. 1A is a schematic diagram of a typical manufacturing paradigm used by a typical biologic manufacturing facility.
Figure 1B:
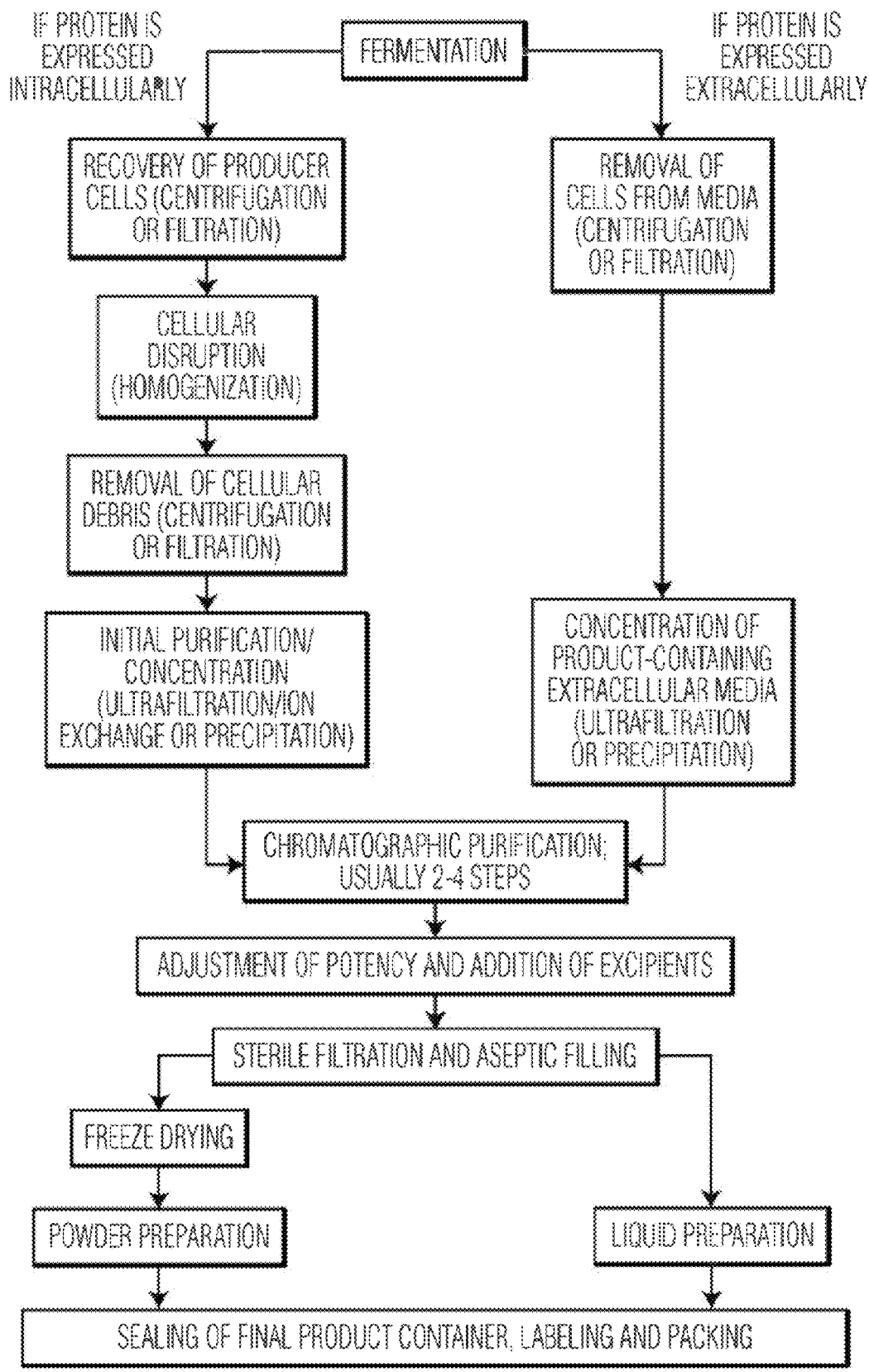
FIG. 1B shows a typical flow sheet for the manufacturing of protein biologics, both for proteins that are expressed intracellularly and proteins expressed extracellularly.
Figure 2:
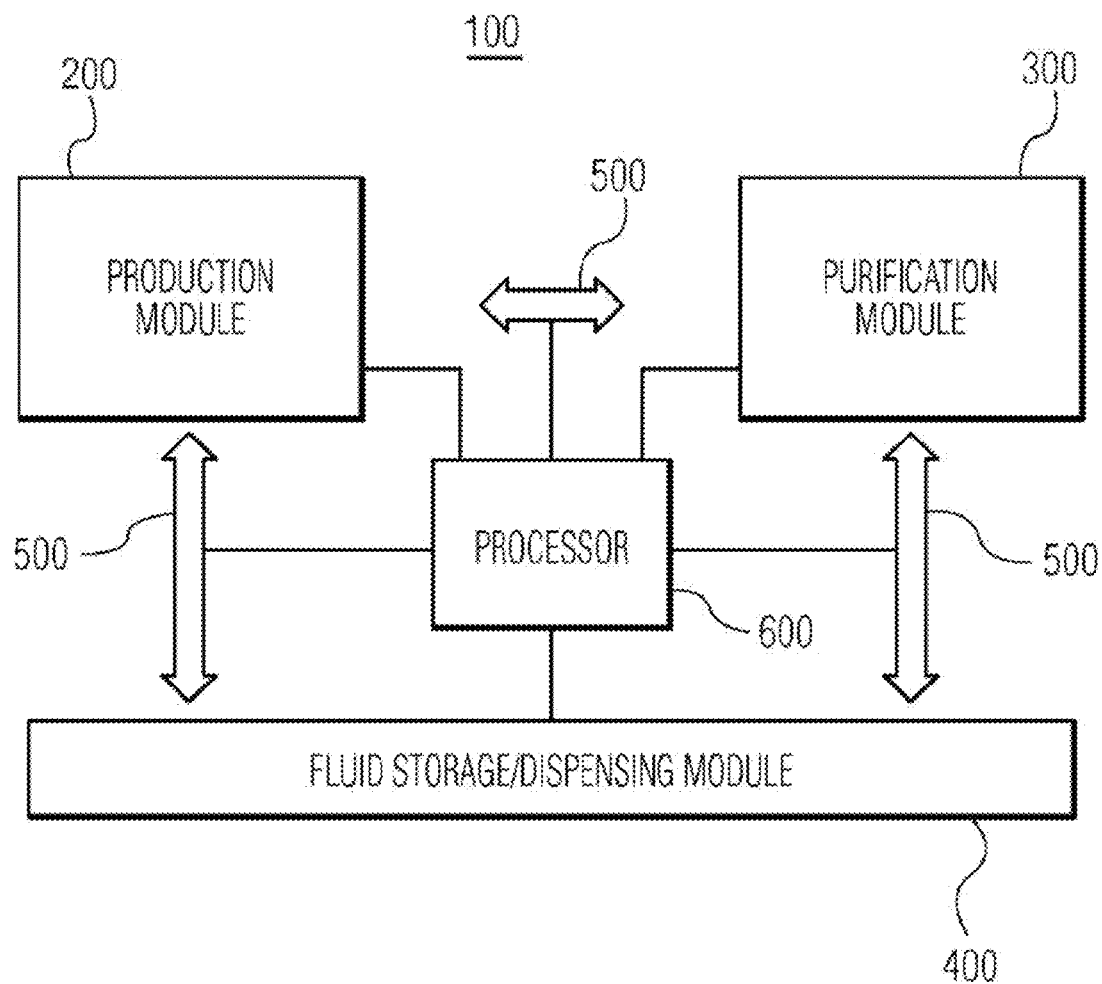
FIG. 2 is a block diagram that illustrates the principles of operation of one preferred embodiment of the present invention.

FIG. 2 is a block diagram that illustrates the principles of operation of one preferred embodiment of the present invention. The bioprocessing system 100 includes a production module 200, a purification module 300 and a fluid storage/dispensing module 400 that are fluidly coupled via coupling components 500. A processor 600 may be in electrical communication with one or more of the production module 200, purification module 300, coupling components 500 and fluid storage/dispensing module 400 for controlling and monitoring the operation of the system 100.

The fluid storage/dispensing module 400 is adapted to store the solutions needed for the production of a protein. The fluid storage/dispensing module 400 may also include containers for storing any waste product produced during the production of the protein. The fluid storage/dispensing module 400 may be temperature controlled, if needed, to maintain the solutions at a required temperature.

The production module 200 is adapted to receive the solutions required for production of a protein, such as a therapeutic protein, from the fluid storage/dispensing chamber via coupling components 500. The production module 200 may suitably include a bioreactor adapted for maintaining living cells that incorporates non-invasive optical chemical sensing technology for monitoring culture parameters (e.g., pH, oxygen, optical density, fluorescence, absorbance, redox, temperature, etc.), such as the bioreactors and optical chemical sensing technology illustrated and described in commonly assigned and related U.S. Pat. Nos. 6,673,532 and 7,041,493, as well as co-pending commonly assigned and related patent application Ser. No. 12/991,947, whose disclosures are incorporated by reference herein in their entirety. These types of bioreactors are particularly suited for cell-based production of therapeutic proteins. Alternatively, the production module 200 may suitably include a stirred mini-reactor such as, for example, the BioGenie Minibioreactor sold by Scientific Bioprocessing, Inc., that is adapted for the cell-free production of a protein, and that are also equipped with sensors for monitoring reaction parameters (e.g., pH, oxygen, optical density, fluorescence, absorbance, redox, temperature, etc.).

After the reaction is complete, the raw product is then transferred to the purification module 300 via coupling components 500. The purification module 300 contains the necessary purification components for purifying the protein from the reagents. The purification module 300 can include, for example, chromatography components and dialyses components for purifying the biologic. The chromatography components can be any type of chromatography components known in the art, including membrane chromatography components and column chromatography components.

The production module 200 and the purification module 300 may each include sensors for monitoring reaction parameters and/or product quality parameters. The parameters monitored can include, but are no limited to, conductivity, temperature, pH, oxygen and $CO_2$. The sensors may be any type of invasive sensor known in the art for monitoring these parameters, where the sensors are in contact with the process fluid. In addition, the sensors may be non-invasive optical chemical sensors, such as those described in U.S. Pat. Nos. 6,673,532 and 7,041,493, and U.S. patent application Ser. No. 12/991,947. In addition, spectrometers known in the art can be used in the production module 200 and/or the purification module 300 to monitor the product stream and/or the inputs to each module. The parameters measured by such spectrometers can include, but are not limited to, absorbance, fluorescence, Raman scattering, circular dichroism and infrared spectral characteristics.

Figure 3:
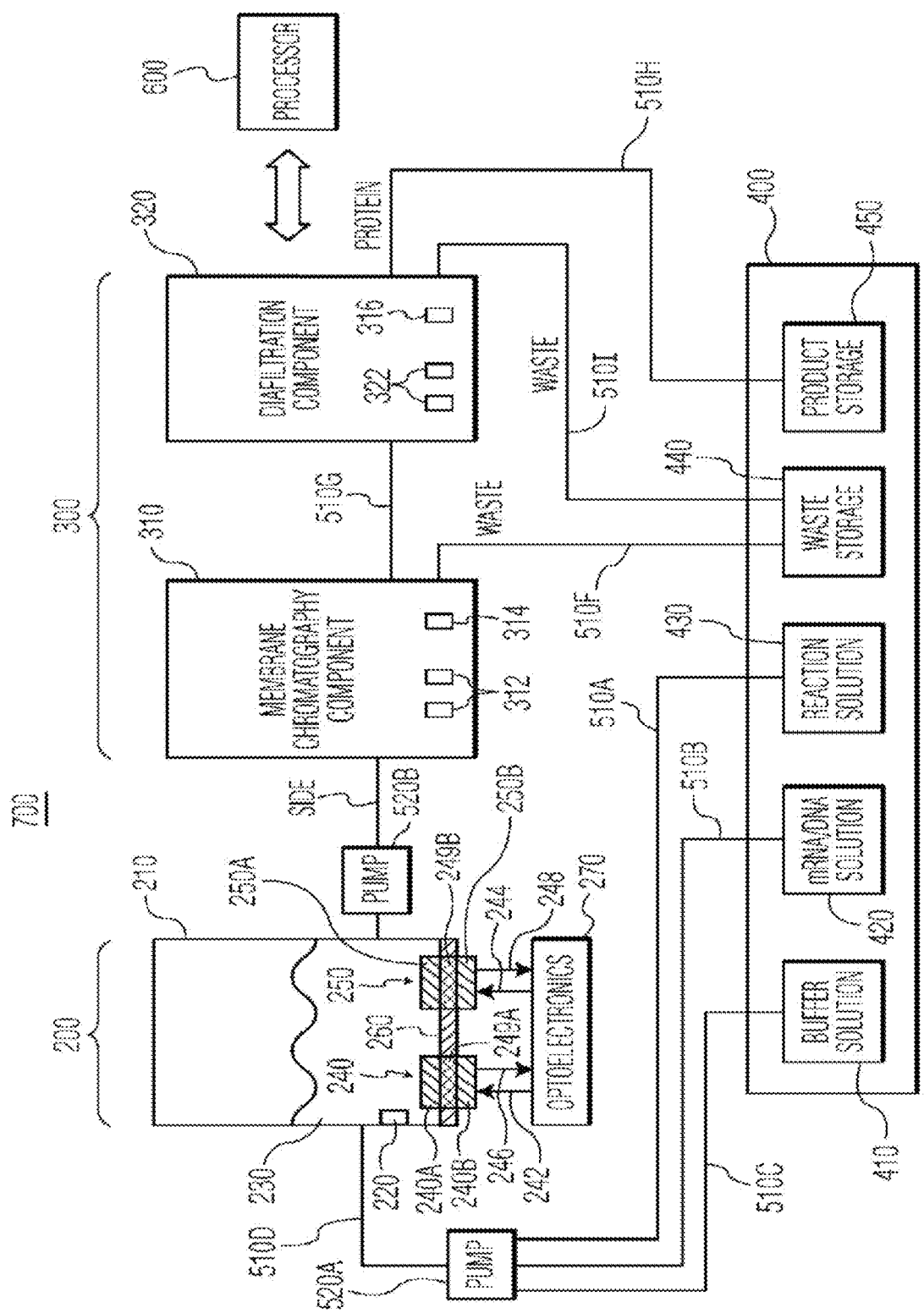
FIG. 3 is a schematic diagram of a bioprocessing system, in accordance with another preferred embodiment of the present invention.

FIG. 3 is a schematic diagram of a bioprocessing system 700, in accordance with another preferred embodiment of the present invention. The system 700 is particularly suited for the cell-free production of proteins and will be described in this context.

The system 700 includes a reactor 210, in which protein expression takes place, a chromatography component 310, a diafiltration component 320 and a fluid storage/dispensing module 400. The reactor 210 preferably includes a heating and cooling element 220, suitably a thermoelectric cooler, for controlling the temperature of the solution 230 inside the reactor 210. The reactor also preferably includes sensors 240 and 250 for monitoring parameters in the reactor solution 230, such as pH, oxygen, redox, conductivity or any other parameter that can be measured with existing sensors. The sensors 240 and 250 can be implemented with any type of sensor known in the art for measuring the desired parameters. However, the sensors 240 and 250 are preferably non-invasive optical chemical sensors. The chromatography components can be any type of chromatography components known in the art, including membrane chromatography components and column chromatography components.

The system 700 also includes a processor 600 that is in communication with one or more of the reactor 210, optoelectronics 270, membrane chromatography component 310, diafiltration component 320, fluid storage/dispensing module 400 and pumps 520A and 520B for controlling and/or monitoring the operation of the system 700.

Optoelectronics 270 are provided for exciting the optical chemical sensors 240 and 250 with excitation light 242 and 244, respectively, and for receiving and detecting emission light 246 and 248 from the optical chemical sensors 240 and 250, respectively. As discussed above, commonly assigned and related U.S. Pat. Nos. 6,673,532 and 7,041,493, as well as co-pending commonly assigned and related U.S. Parent application Ser. No. 12/991,947 describe in more detail how non-invasive optical chemical sensing technology can be used to monitor parameters.

In FIG. 3, two optical chemical sensors 240 and 250 are shown, and are preferably adapted to measure pH and dissolved oxygen, respectively. However any number of optical chemical sensors (including only one) may be used depending on the number and type of parameters being measured. Optoelectronics 270 include optical excitation sources (not shown) for generating the excitation light 242 and 244, as well as photodetectors (not shown) for detecting the emission light 246 and 248 from the optical chemical sensors 240 and 250. The type of optical excitation source or sources used in optoelectronics 270 are matched to the types of optical chemical sensors 240 and 250 used in the reactor 210. Any combination of optical excitation sources and optical chemical sensors may be used, depending on the number and types of parameters being measured. Examples of optical excitation sources that can be used included in optoelectronics 270 include, but are not limited to, light emitting diodes and laser diodes. Alternatively, the optoelectronics 270 may just be used to measure optical properties of the reactor contents in their entirety absent any sensors.

Further, for each optical chemical sensor 240 and 250, two possible placements on the reactor 210 are shown. The two possible placements for optical chemical sensor 240 are shown as 240A and 240B. The two possible placements for optical chemical sensor 250 are shown as 250A and 250B.

In the "A" placement (240A and 250A), the optical chemical sensors 240A and 250A are positioned inside the reactor 210 on a reactor wall 260. With this placement, the optical chemical sensors 240A and 250A are in physical contact with the solution 230, and the reactor wall 260 on which the optical chemical sensors 240A and 250A are placed is optically transparent to the excitation light 242 and 244, so that the excitation light can reach the optical chemical sensors 240A and 250A.

In the "B" placement (240B and 250B), the optical chemical sensors 240B and 250B are positioned outside the reactor 210 on reactor wall 260. With this placement, the thickness of the reactor wall 260 is sufficiently small so as to allow the analytes that are being measured to diffuse through the reactor wall 260 and contact the optical chemical sensors 240B and 250B. Alternatively, the portions of the reactor wall 260 on which the optical chemical sensors 240B and 250B are attached can replaced with barrier membranes 249A and 249B that are adapted to allow the analytes being measured to diffuse therethrough so that they come in contact with optical chemical sensors 240B and 250B. The use of barrier membranes and thin reactor walls to effectuate diffusion of the analytes of interest through a container wall to optical chemical sensors is described in more detail in commonly assigned and related U.S. patent application Ser. No. 13/378,033, which is incorporated herein by reference in its entirety.

In the FIG. 3 embodiment, the fluid storage/dispensing module 400 preferably includes a buffer solution container 410 for holding buffer solution, an mRNA/DNA solution container 420 for holding mRNA/DNA solution, a reaction solution container 430 for holding reaction solution, a waste storage container 440 for holding waste solution and a product storage container 450 for holding the purified protein. In operation, reaction solution, mRNA/DNA solution and buffer solution are directed to reactor 210 via conduits 510A, 510B, 510C and pump 520A.

After the reaction in the reactor 210, the raw product is directed to membrane chromatography component 310 via conduit 510E and pump 520B for purification of the protein from the reagents. Membrane chromatography component 310 may suitably include a cylindrically shaped housing which contains porous membrane layers (preferably at least 10 porous membrane layers), where the individual membranes consist of an appropriate polymer, such as polymethacrylate, that has been chemically functionalized with a ligand, such as a diethylaminoethyl (DEAE), a quaternary amine (Q), or a carboxymethyl (CM) ligand for the case of ion-exchange chromatography, or a phenyl or butyl ligand for the case of hydrophobic interaction chromatography, or a mercaptoethylpyridine (MEP) ligand for the case of mixed mode chromatography. One preferred embodiment of the membrane chromatography component 310 will be discussed in more detail below in connection with FIG. 5. Waste from the membrane chromatography process is directed to waste storage container 440 via conduit 510F. The purified product is directed to diafiltration component 320 for dialysis via conduit 510G and pump 520C.

Membrane chromatography component 310 may also include one or more sensors 312 for monitoring product quality parameters, such as conductivity, temperature, pH, oxygen, $CO_2$, absorbance, fluorescence, Raman, circular dichroism and infrared spectral characteristics. The sensors 312 may be any type of invasive or noninvasive sensor known in the art for measuring these parameters including, but not limited to, spectrometers. In addition, the sensors may be non-invasive optical chemical sensors, such as those described in U.S. Pat. Nos. 6,673,532 and 7,041,493, and U.S. patent application Ser. No. 12/991,947. In addition, membrane chromatography component 310 preferably includes a heating and cooling element 314, suitably a thermoelectric cooler, for controlling the temperature of the solution (raw product) inside the membrane chromatography component 310.

The diafiltration component 320 may suitably include a hydrophilic polymeric membrane, such as a polyethersulfone, a cellulosic, or a polyvinylidene fluoride (PVDF) membrane with a well defined pore structure that yields a desired molecular weight cut-off (MWCO) value in the range of 10 k to 200 k Da as appropriate for a given application. The final protein that comes out of the diafiltration component 320 is directed to product storage container 450 via conduit 510H. The waste product produced from the dialysis process in the diafiltration component 320 is directed to waste storage container 440 via conduit 510I.

Diafiltration component 320 may also include one or more sensors 322 for monitoring product quality parameters, such as conductivity, temperature, pH, oxygen, $CO_2$, absorbance, fluorescence, Raman, circular dichroism and infrared spectral characteristics. The sensors 322 may be any type of invasive or noninvasive sensor known in the art for measuring these parameters including, but not limited to, spectrometers. In addition, the sensors may be non-invasive optical chemical sensors, such as those described in U.S. Pat. Nos. 6,673,532 and 7,041,493, and U.S. patent application Ser. No. 12/991,947.

In addition, diafiltration component 320 preferably includes a heating and cooling element 316, suitably a thermoelectric cooler, for controlling the temperature of the solution (raw product) inside the membrane chromatography component 320.

In addition to the pumps 520A, 520B and 520C, any number of valves or other hydraulic components, such as additional pumps, may be used throughout the system 700 to assist in controlling the flow of solution/product between the various components of the system 700.

Figure 4:
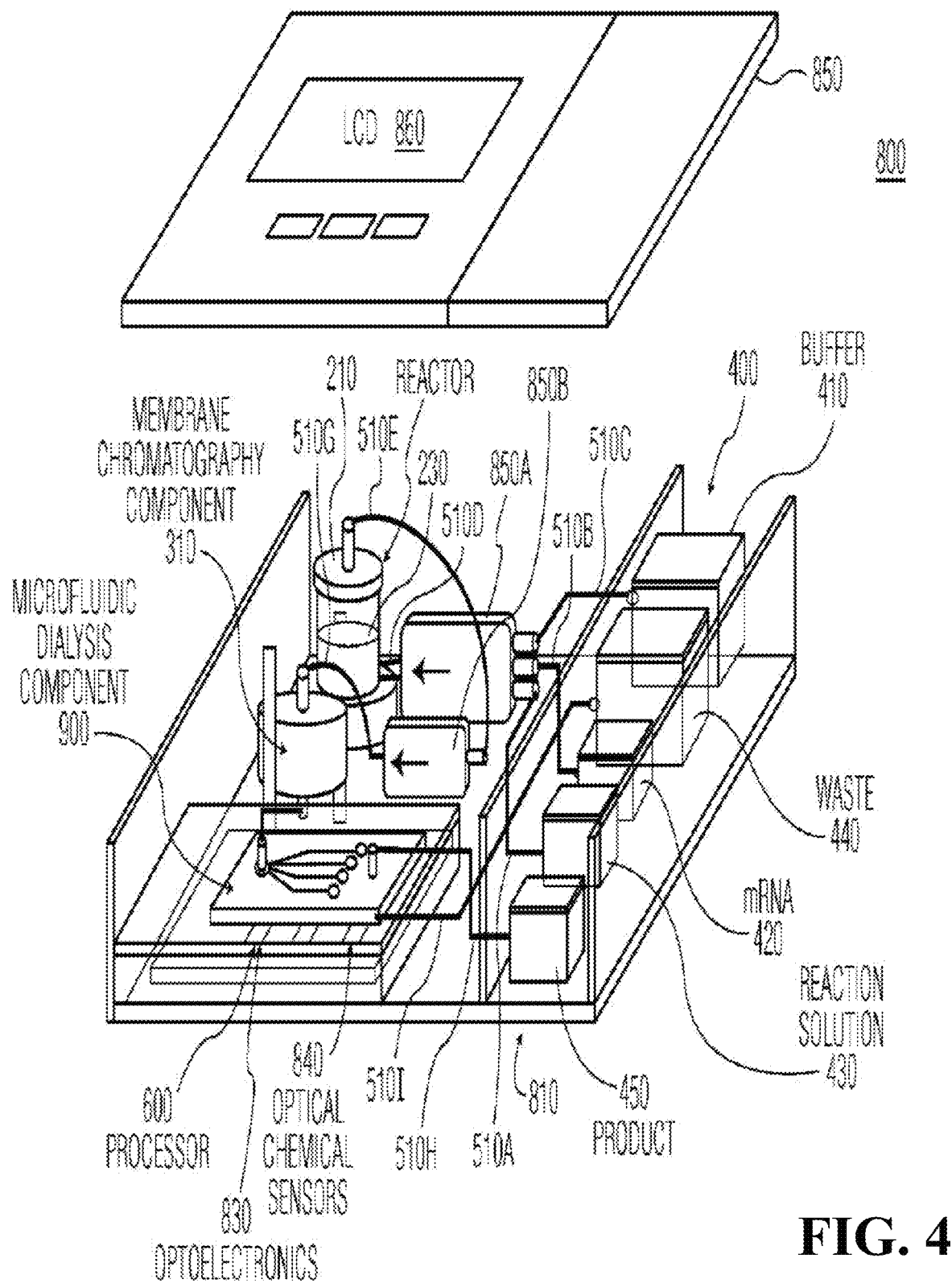
FIG. 4 is a schematic diagram of a microscale bioprocessing system, in accordance with another embodiment of the present invention.

The present invention is particularly suited to miniaturization by using micropumps and microfluidic technology. FIG. 4 is a schematic diagram of a microscale bioprocessing system 800, in accordance with another embodiment of the present invention. The system 800 includes many of the same components of the system 700 of FIG. 3, and common elements are labeled with common element numbers.

The system 800 contains a fluid storage/dispensing module 400 that includes a buffer solution container 410 for holding buffer solution, an mRNA/DNA solution container 420 for holding mRNA/DNA solution, a reaction solution container 430 for holding reaction solution, a waste storage container 440 for holding waste solution and a product storage container 450 for holding the purified protein. The system 800 also includes a reactor 210, a membrane chromatography component 310, a diafiltration component 820, a processor 600, optical chemical sensors 840 chosen and positioned to monitor finished product quality parameters, such as, for example, conductivity, redox, pH, UV spectrum and protein concentration, and optoelectronics 830 for providing optical excitation light and for detecting emission light from the optical chemical sensors 840. The optoelectronics 830 may also just be used to measure the optical properties of the finished product absent any sensors.

The reactor 210 can be of any size, but in the microscale embodiment of FIG. 4, it preferably has a volume capacity of less than approximately 50 milliliters, and more preferably approximately 20 milliliters or less, in order to keep the system 800 relatively compact. The reactor 210 may be implemented, for example, with the BioGenie minibioreactor system manufactured by Scientific Bioprocessing, Inc.

Micropumps 850A and 850B and conduits 510A-510I direct solution to the various components in a manner similar to pumps 520A, 520B and conduits 510A-510I in the system 700 of FIG. 3. Although not shown in FIG. 4, the reactor 210 contains optical chemical sensors and optoelectronics for monitoring parameters in the reactor solution 230 in a manner similar to system 700 of FIG. 3. The micropumps 850A and 850B may be implemented with any type of micropump known in the art such as, for example, the mp5 micropump or the mp6 micropump manufactured by Bartels Mikrotechnik.

The housing lid 850 may contain a display, such as an LCD display 860, that connects to the processor 600 and that can provide information about the system 800, such as, for example, diagnostic information, reaction parameters and/or finished product quality parameters, such as, for example, conductivity, redox, pH, UV spectrum and protein concentration.

The processor 600 in FIGS. 2, 3 and 4 may be implemented with a general purpose desktop computer or a general purpose laptop computer. In addition, the processor may be implemented with a tablet computer or smartphone, such as iOS or Android-based tablets and smartphones. However, processor 600 can also be implemented with a special purpose computer, programmed microprocessor or microcontroller and peripheral integrated circuit elements, ASICs or other integrated circuits, hardwired electronic or logic circuits such as discrete element circuits, programmable logic devices such as FPGA, PLD), PLA or PAL or the like. In general, any device on which a finite state machine capable of executing code for implementing the functionality described herein can be used to implement the processor 600.

Figure 5:
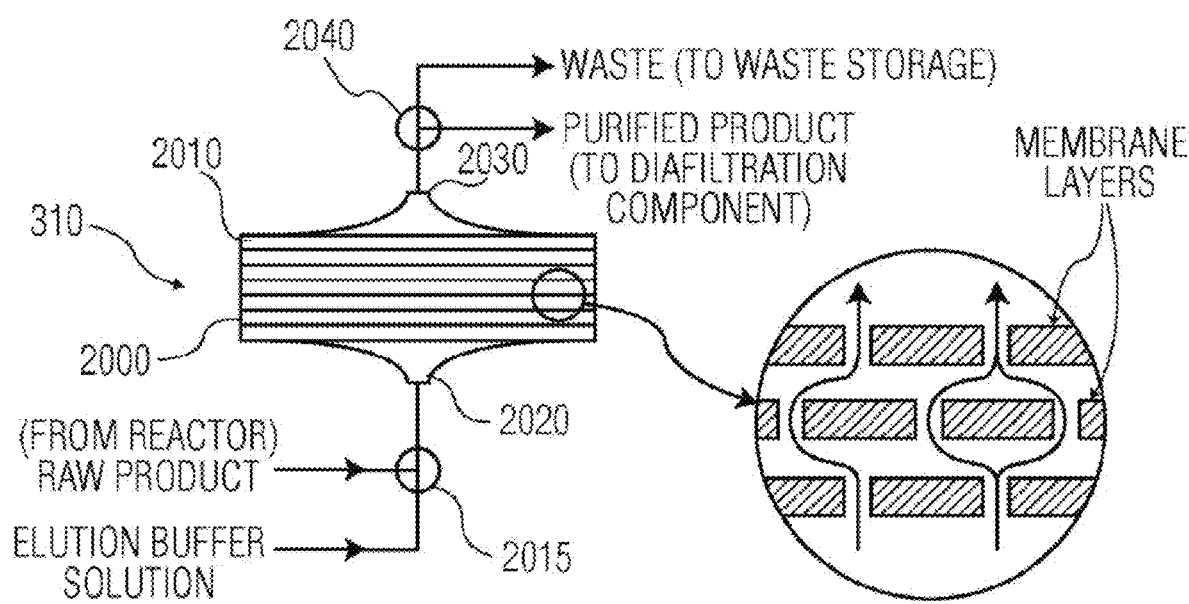
FIG. 5 is a side schematic view of a membrane chromatography component that can be used in the systems of FIGS. 3 and 4, in accordance with one embodiment of the present invention.

FIG. 5 shows a membrane chromatography component 310 that can be used in systems 700 and 800, in accordance with one preferred embodiment of the present invention. The membrane chromatography component 310 includes a housing 2000 and porous membrane layers 2010 (preferably at least 10 porous membrane layers). As discussed above, the individual porous membrane layers 2010 preferably consist of an appropriate polymer, such as polymethacrylate, that has been chemically functionalized with a ligand, such as a diethylaminoethyl (DEAE), a quaternary amine (Q), or a carboxymethyl (CM) ligand for the case of ion-exchange chromatography, or a phenyl or butyl ligand for the case of hydrophobic interaction chromatography, or a mercaptoethylpyridine (MEP) ligand for the case of mixed mode chromatography.

The membrane chromatography component 310 can be of any size, but in the microscale embodiment of FIG. 4, it preferably has a volume capacity of less than approximately 100 milliliters, and more preferably less than approximately 5 milliliters, in order to keep the system 800 relatively compact. The membrane chromatography component 310 may be implemented, for example, with a SARTOBIND® Q SingelSep Nano manufactured by SARTORIUS STEDIM BIOTECH®, which has a bed volume of 1 ml and a membrane area of 36 $cm^2$.

Raw product from reactor 210 is mixed with elution buffer solution via three-way valve 2015, and the mixture enters the membrane chromatography component 310 via inlet 2020. Purified product and waste exits via the outlet 2030.

Three-way valve 2040 directs the purified product to the diafiltration component 320/900/1100 and directs the waste to waste storage 440.

Figure 6A:
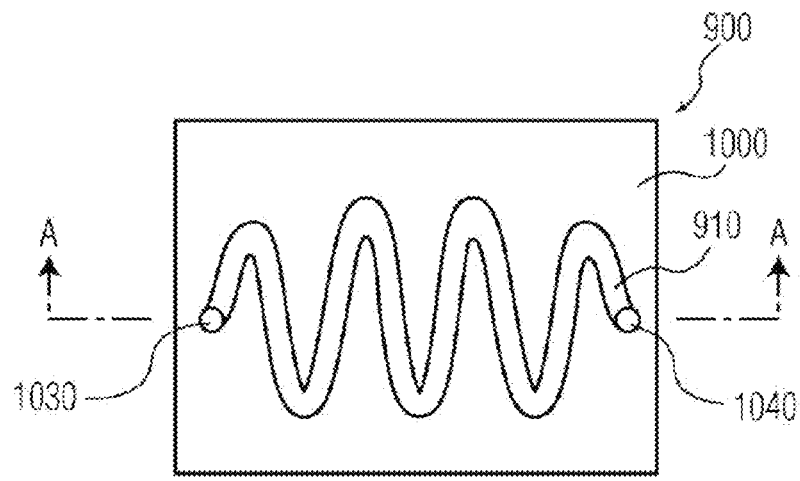
FIG. 6A is a top plan view of a microfluidic diafiltration component that can be used in the systems of FIGS. 3 and 4, in accordance with one embodiment of the present invention.
Figure 6B:
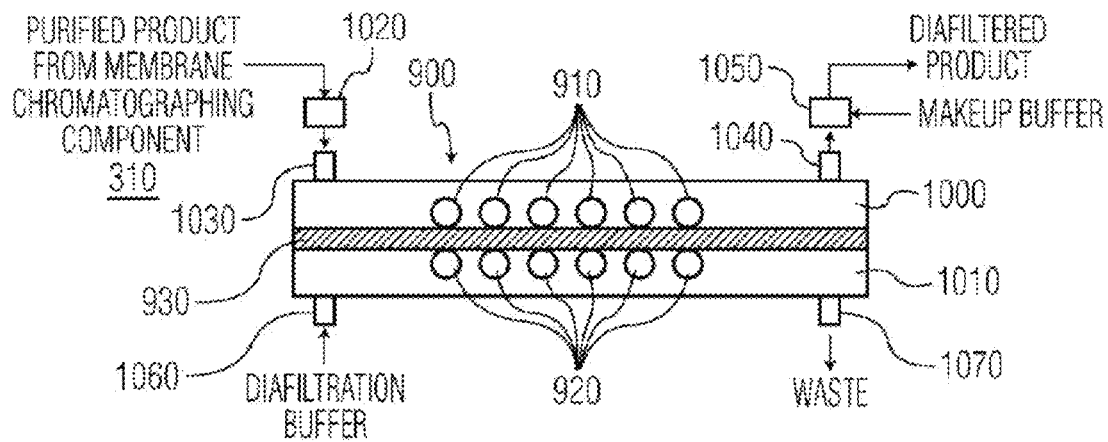
FIG. 6B is a schematic cross-sectional view of the equilibrium chamber of FIG. 6A looking along the cross-section line A-A of FIG. 6A.
Figure 6C:
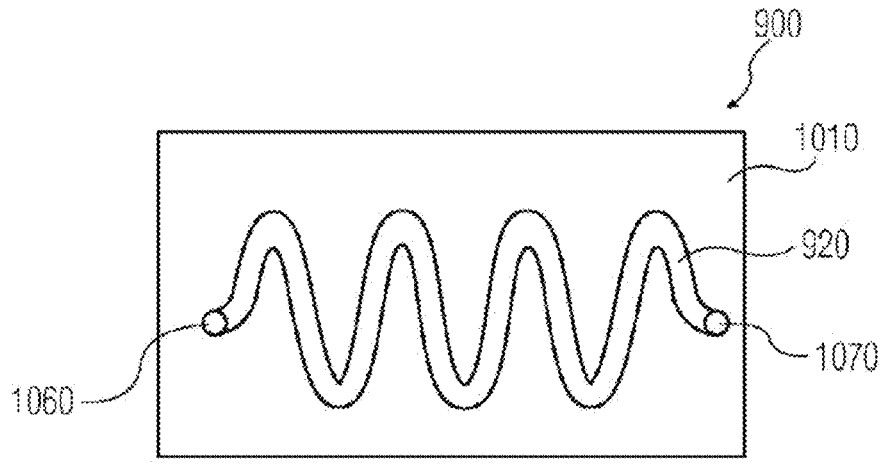
FIG. 6C is a bottom plan view of the equilibrium chamber of FIG. 6A.

FIGS. 6A-6C show a diafiltration component 900 that can be used in systems 700 and 800, in accordance with one preferred embodiment of the present invention. The diafiltration component 900 includes serpentine-shaped product and buffer sections 910 and 920, respectively. The diafiltration component 900 of FIGS. 6A-6C include a product section 910 that is a serpentine-shaped channel formed on a first substrate 1000. Similarly, the buffer section 920 is a channel formed on a second substrate 1010 with the same serpentine shape as the product section 910. A diafiltration membrane 930 is sandwiched between the first and second substrates 1000 and 1010, such that the serpentine-shaped channels that form the product and buffer sections 910 and 910 substantially overlap each other. The substrates 1000 and 1010 are attached to each other, with the diafiltration membrane 930 sandwiched between them, with any adhesive known in the art.

In the diafiltration component 900 of FIGS. 6A-6C, a diafiltration buffer solution flows through the serpentine-shaped product section 920 and purified product from the membrane chromatography component 310 flows through the serpentine-shaped product section 910. Diffusion takes place from the product section 910 to the counterpart, similarly shaped buffer section 920 via the diafiltration membrane 930.

The purified product from the membrane chromatography component 310 enters the product section 910 via inlet buffer reservoir 1020 and inlet 1030. The diafiltered product exits the product section 910 via outlet 1040 and outlet buffer reservoir 1050. Diafiltration buffer enters the buffer section 920 via inlet 1060 and exits the buffer section via outlet 1070. The diafiltration buffer is chosen to facilitate the transfer of components through the diafiltration membrane 930, and could be, for example, 25 millimolar phosphoric acid titrated to pH 7 with sodium hydroxide, or 25 millimolar citric acid tritrated to pH 5 with sodium hydroxide.

The inlet and outlet buffer reservoirs 1020 and 1050 are optionally used in order to dampen the back-and-forth oscillating flow, if needed. A makeup buffer solution is preferably added to the diafiltered product via the outlet buffer reservoir 1050 in order to replace the fluid that was that passed through the diafiltration membrane 930 with an equivalent volume of a different type of buffer, thereby transferring the protein of interest to the makeup buffer. Alternatively, the volume of the makeup buffer added via the outlet buffer reservoir 1050 can be less than the volume of fluid that has passed through the diafiltration membrane 930, in which case the diafiltration component 900 accomplishes both buffer exchange and protein concentration.

As discussed above, diafiltration membrane 930 may suitably be a hydrophilic polymeric membrane, such as a polyethersulfone, a cellulosic, or a polyvinylidene fluoride (PVDF) membrane with a well defined pore structure that yields a desired molecular weight cut-off (MWCO) value in the range of 10 k to 200 k Da as appropriate for a given application.

Figure 7:
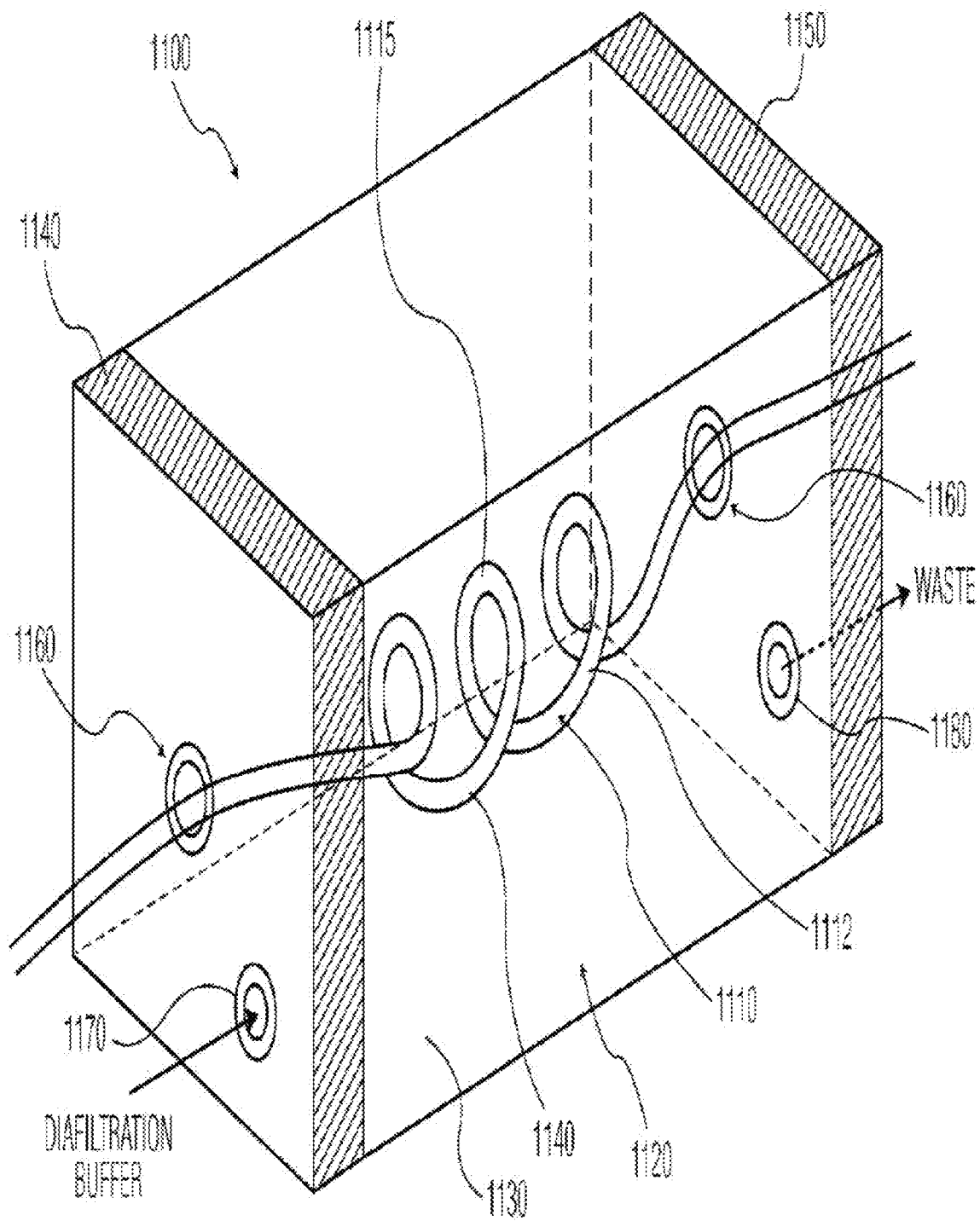
FIG. 7 is a perspective schematic view of another microfluidic diafiltration component that can be used in systems of FIGS. 3 and 4, in accordance with on embodiment of the present invention.

FIG. 7 shows a diafiltration component 1100 in accordance with another embodiment of the present invention. The diafiltration component 1100 may be used in system 700 or system 800 of FIGS. 3 and 4, respectively. The diafiltration component 1100 includes a buffer section 1120, and a product section 1110 that comprises tubing 1112 that is passed through the buffer section 1120. The tubing 1112 that makes up the product section 1110 can be any type of tubing known in the art that can function as the dialysis membrane 1140 between the product 1115 in the product section 1110 and the buffer 1130 in the buffer section 1120.

The tubing 1112 is preferably flexible so that a larger amount of tubing can be placed inside the solvent section 1120. The more tubing 1112 is present in the buffer section 1120, the more diffusion can take place between the tubing 1112 and the buffer 1130 due to the larger tubing surface area in contact with the buffer 1130. End portions 1140 and 1150 of the diafiltration component 1100 contain openings 1160 for the tubing 1112 to enter and exit the diafiltration component 1100. The end portions 1140 and 1150 also contain an inlet 1170 for receiving diafiltration buffer solution, and an outlet 1180 for expelling used diafiltration buffer solution (waste). Although the diafiltration component 1100 is shown as rectangularly-shaped, it can be any other shape, such as cylindrically-shaped. Further, the diafiltration component 1100 can suitably be a flow cell that has been modified to pass the tubing 1112 through the buffer section 1120.

Cell-Free Expression of Glucose Binding Protein

The systems and methods of the present invention can be used, for example, for the cell-free expression and purification of glucose binding protein (GBP). Glucose is a major carbon and energy source in cellular metabolism of animal body and in bioprocess industry. Glucose is not always beneficial in bioprocesses, it could also be detrimental in bacterial culture leading to self lysis of cells by formation of acetate in Krebs cycle and reducing the pH of the culture. Thus, fast and efficient concentration detection of glucose is is desired.

Glucose binding protein is a protein which could bind to glucose and serve this purpose by acting as a biosensor. GBP is a monomeric periplasmic protein with molecular weight of 34 kD (kilo Dalton) and is synthesized in the cytoplasm of *E. coli*. GBP binds to glucose with high affinity and could be used as a glucose biosensor. In vivo expression of GBP, which is also a conventional method of protein production, is cumbersome, expensive and time consuming. The present invention can provide a cell free expression and purification system at a small scale which could generate milligrams of quantity in few hours.

A biosensor is an analytical device used for the detection of an analyte that combines a biological component with a physicochemical detector component. GBP is such a biosensor, where GBP binds with glucose and binding is analyzed using fluorescence intensity and the corresponding signal is compared with standard glucose signal to estimate concentration of unknown sample. Using conventional in vivo methods, GBP is expressed in *E. coli* (L255C), followed by osmotic shock, purified by DEAE SEPHADEX™ A-50 column and dialysis using 10 kD membrane. An alternative method is cell-free expression, wherein cellular machinery is used for the protein expression and relatively fewer number of downstream purification operations are required for rapidly producing the desired protein.

In recent years, numerous proteins (12 to 135 kD) were expressed in cell-free systems of *E. coli* and wheat germ with the expression level ranging from a few micrograms to a few milligrams per milliliter in continuous flow cell-free expression mode. A combination of batch and continuous exchange methods have produced protein up to 6 mg/ml in *E. coli* S30 extract at a small scale. For all these protein expressions, reactors operating in different modes were studied with a membrane as an integral part of the system, separating the reaction mixture and feed solution. Continuous flow reactors are advantageous in terms of higher purity of proteins, higher productivity, toxic protein expression, computerization and easy control of the reaction due to the absence of a cell wall barrier. On the other hand, these reactors also pose the challenges of higher complexity and reactor costs, as well as solubility management of protein product.

In another study, expression of a fusion protein consisting of murine GM-CSF (granulocyte macrophage colony stimulating factor) and a scFv antibody, in reactor systems such as thin film, bubble column and Eppendorf tube without membrane, were studied, producing protein up to >500 μg/ml protein with significant amount of precipitated protein (~50%). Recently, rhGM-CF was expressed in a 100 L stirred tank reactor expressing protein upto 700 mg/L which was subsequently purified with DEAE resin, tangential flow filtration membrane (3 kD cut off) and SEPHACRYL™ S-100 size exclusion chromatography with 99% purity and 65% recovery. Cell-free expression has not only been successful in the expression of bacterial proteins, but also successfully produced glycoproteins like human choriogonadotropin (hCG) and envelope glycoprotein (gp 120) of human immunodeficiency virus type-1 (HIV-1) in hybridoma cell extract (HF10B4).

For protein purification, people have relied on column chromatography traditionally, but in recent years membrane chromatography has emerged as an additional aid in this field, eliminating column chromatography at specific steps like capture and polishing of protein at final step with overall cost reduction up to 65%. Column chromatography is still useful for gradient purification of proteins, but membrane chromatography could also be studied by relying on the fact that step elution of protein and removal of the impurities could be done at different buffer conditions.

The chart below compares cell-free and in vivo protein expression systems.

| In vivo | Cell free |
| --- | --- |
| Biological cell required | No cell, but cellular machinery is required |
| Time consuming process | Time effective process |
| Toxic protein could not be expressed | Toxic protein could be expressed |
| Multiple steps in purification required | Relatively less number of steps required |
| Higher fraction of misfolded protein along with folded protein | No misfolded protein reported, but precipitated |
| Higher endotoxins challenge | Relatively less endotoxins challenge |
| Higher amount of impurities in crude protein causing challenges in capture step | Relatively pure, enhancing capture and increasing yield of the protein |
| Established scale up | Has significant potential to scale up |
| Protein expression upto g/l | Protein expression upto mg/l |

Biomolecules for Protein Expression

The following biomolecules are preferably used for protein expression. To carry out a protein expression reaction, energy components and amino acids are supplied externally:

A genetic template for the target protein (mRNA or DNA) expression.

T7 RNA polymerases for mRNA transcription.

9 Translation factors (initiation, elongation and termination).

20 aminoacyl-tRNA synthetases (ARSes) for esterification of a specific amino acid to form an aminoacyl-tRNA.

Methionyl-tRNA transformylase transfers hydroxymethyl-, formyl-groups.

Creatine kinase converts ATP to ADP.

Myokinase catalyzes the inter conversion of adenine nucleotides.

Pyrophosphatase are acid anhydride hydrolases that act upon diphosphate bonds.

4 nucleoside triphosphates (ATP,GTP,CTP,TTP) for DNA formation.

Creatine phosphate serves as a rapidly mobilizable reserve of high-energy phosphates.

10-formyl-5,6,7,8-tetrahydrofolate important in the formylation of the methionyl initiator tRNA (fMet-tRNA).

20 amino acids for protein synthesis.

Ribosomes for polypeptide translation.

46 tRNAs in protein synthesis.

Cellular components which assist in proper protein folding.

Mechanism of Protein Expression in In vivo and Cell-Free Systems

Figure 8:
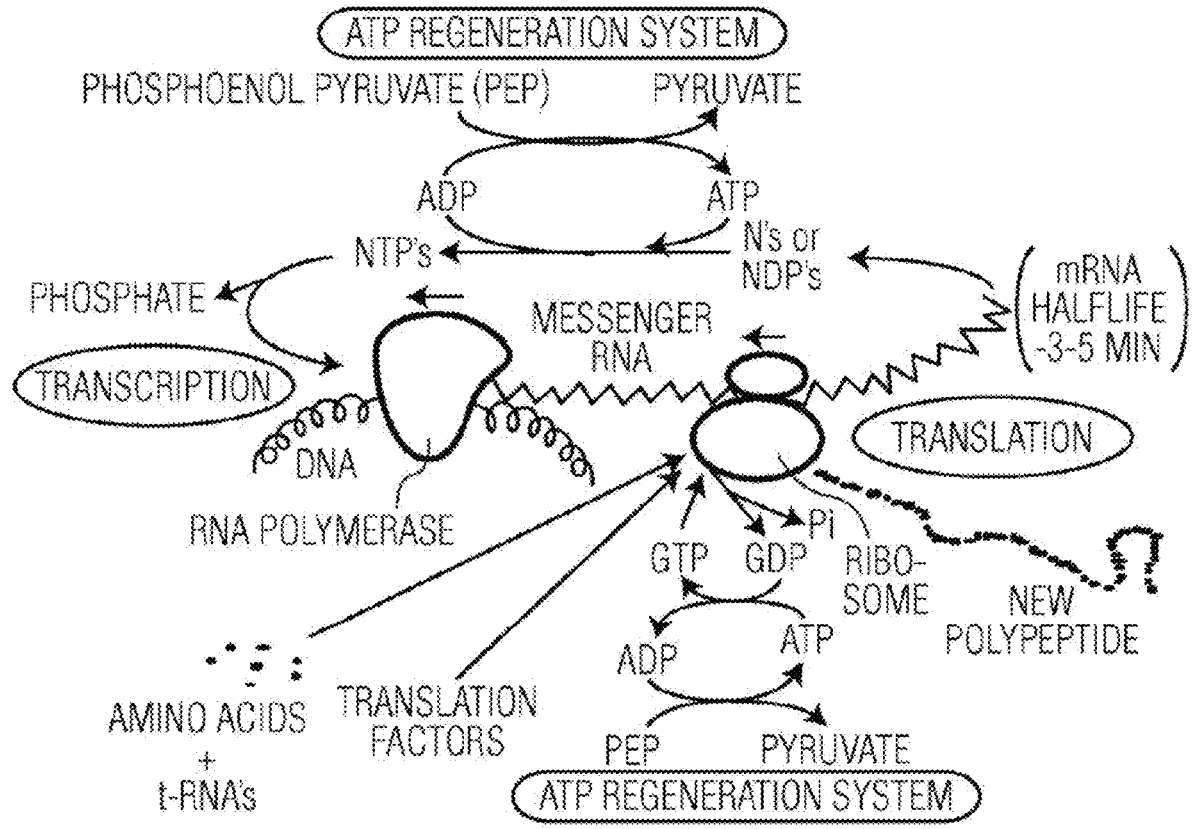
FIG. 8 is a diagram showing the main steps in in vivo protein expression, in accordance with one embodiment of the present invention.

Protein is expressed in three main steps involving replication, transcription and translation, as shown in FIG. 8. With regards to the replication step, the blueprints for proteins are stored in cell's DNA. DNA multiplies to make multiple copies by a process called replication. DNA polymerase is an enzyme that synthesizes new DNA by adding new nucleotides along with other proteins which are associated with the fork and assist and continuation of DNA synthesis.

Transcription occurs in three steps in both prokaryotes and eukaryotes: Initiation, Elongation and Termination. The initiation of transcription occurs when the double-stranded DNA is unwound to allow the binding of RNA polymerase. Once transcription is initiated, the RNA polymerase is released from the DNA. Transcription is regulated at various levels by activators and repressors, and also by chromatin structure in eukaryotes.

In prokaryotes, no special post-transcriptional modification of mRNA is required. However, in eukaryotes, mRNA is further processed to remove introns (splicing), to add a 'cap' (M7 methyl-guanosine) at the 5' end and to add multiple adenosine ribonucleotides at the 3' end of mRNA to generate a poly(A) tail. The modified mRNA is then translated.

The translation or protein synthesis is also a multi-step process with Initiation, Elongation and Termination steps and is similar in both prokaryotes and eukaryotes. The process requires cellular components such as ribosomes, transfer RNAs (tRNA), mRNA and protein factors as well as small molecules like amino acids, ATP, GTP and other cofactors.

Cell-Free Protein Expression from an Engineer's Perspective

Cell extract is prepared after cell lysis and removal of cell wall. Protein could be synthesized using DNA or mRNA template by adding into the cell extract. When DNA is used as template (i.e. linked reaction), it first transcribes to mRNA in the presence of translation mixture and protein is expressed. Alternatively mRNA could also be used for this purpose. Another way of protein expression is the coupled reaction where transcription and translation reactions are carried out in the same tube with all necessary components for both reactions. In either case, mRNA is ultimately translated in the cell extracts without the need for purification of the message.

Conventional and Non-Conventional Method of GBP Production

In the conventional method, GBP is produced in multiple steps like pre-inoculation of *E. coli* mutants (L225C.) in Luria Bertani (LB) broth, culturing, harvesting, cell washing, osmotic shock, labeling, liquid chromatography and dialysis. All these steps are time consuming (around 4 days) and cumbersome. The present invention enables a non-conventional cell free expression of GBP where expression is faster and the resulting protein is relatively pure. This protein would preferably be labeled using a fluorophore called acrylodan (6-Acryloyl-2dimethylaminonaphthalene) and purified by D15 (DEAE) chromatography membrane. The protein would preferably further be concentrated and dialyzed against 5 mM tris-HCl, pH 7.5.

Human Blood as the Source of Cell Extracts

In one embodiment of the present invention, human blood is used as the source of cell extracts for the manufacture of therapeutic proteins using the systems described above and illustrated in FIGS. 2-7. Blood collection/banking/transfusion is a well-established, safe practice. An estimated 5 million Americans receive blood transfusions each year and there is a vast infrastructure in place to draw, process, store and distribute blood. This infrastructure can be leveraged and used a source of cell extracts for therapeutic protein manufacturing.

The majority of the cells in blood are erythrocytes, which conveniently have no nucleus. Around 0.5-2% of all cells are reticulocytes, which are immature blood cells that are rich in ribosomal RNA. Other cells (i.e., lymphocytes) may also be used for the production of cell extracts. The blood source may be screened donor blood that is routinely used for transfusions. However, the cell extracts are preferably obtained from the blood of the patient that will be receiving the produced therapeutic protein. Blood extracted from the patient is preferably combined with the therapeutic protein that is produced from the extracted blood, which is then injected back into the patient with little to no immune response.

Since the cell extracts used to manufacture the therapeutic protein come from the patient, the regulatory approvals for injecting the therapeutic proteins back into the patient will be far simpler to obtain. Furthermore, blood transfusions are currently regarded as an extremely safe practice due to the success of screening and processing of blood components. Blood is continually recycled in the body and broken down, so reintroducing fractionated blood components back into the body should be safe.

Such an approach completely removes economics from the equation as patient specific medicine can be produced at the same cost, regardless if, for example, the end product is insulin, a clotting factor or an orphan drug. All that is needed is the cDNA for the desired therapeutic protein. The entire human genome cDNA is readily available.

Exciting possibilities can be readily tried out with very little safety risk. For example, recent papers suggest that young mouse blood has proteins that alleviate symptoms of aging and Alzheimer's disease when injected into older mice. A single protein, GDF11 appears to increase endurance. With the systems and methods of the present invention, one can now simply use an older patient's blood extract and produce "fountain of youth" proteins in it and assess efficacy. This is but one example of various clinical trials that can be attempted, and is in sharp contrast to stem cells and other regenerative medicine and gene therapy approaches where one has limitations in controlling the fate of the transplanted cells.

In the event of a natural or man-made disaster, relying on a centralized drug/vaccine manufacturing paradigm is a serious vulnerability to public health. The present invention will empower hospitals, clinics and eventually patients themselves to make their own medicines.

Figure 9:
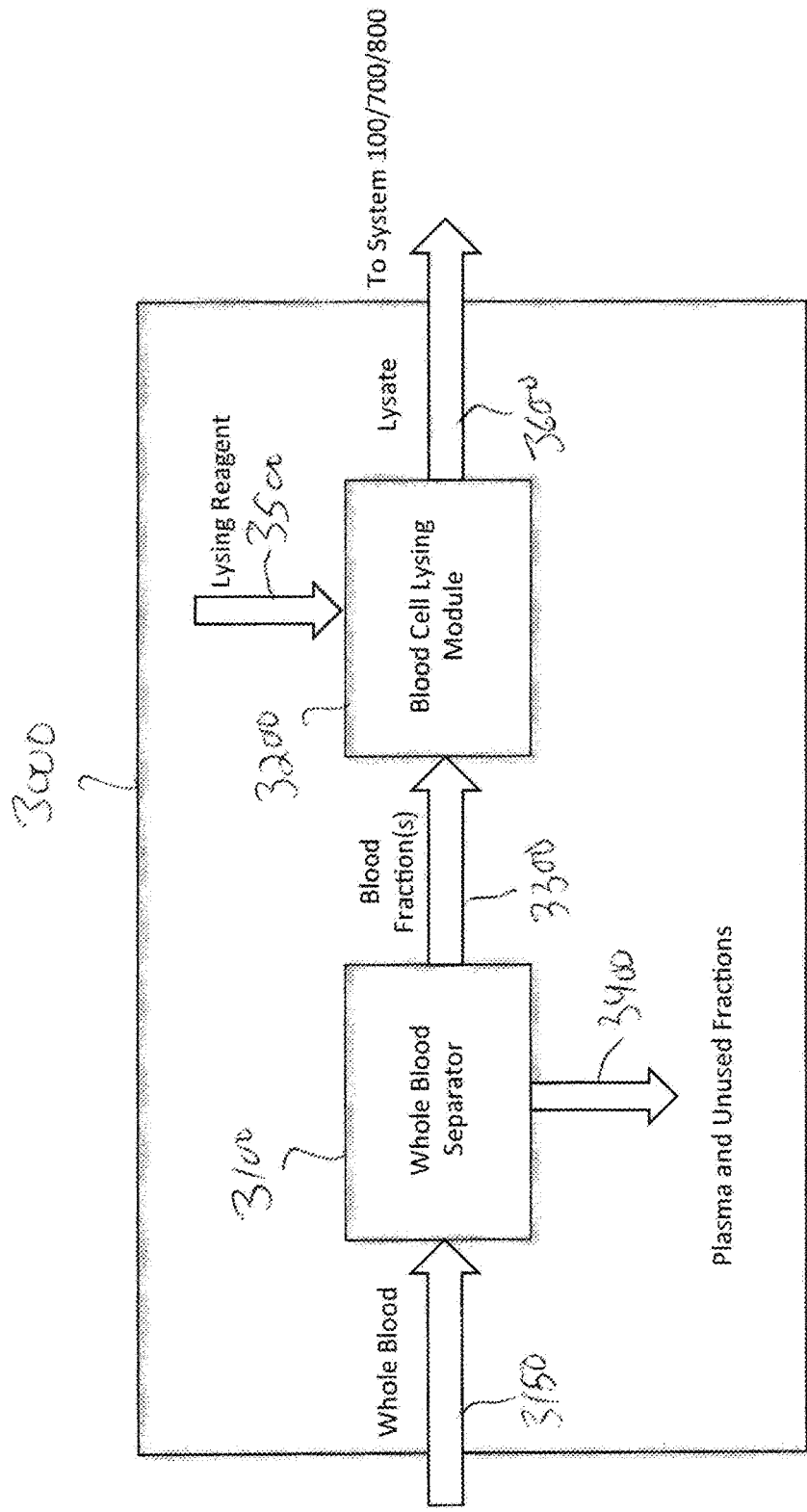
FIG. 9 is a block diagram of a cell extraction module for extracting cells from human blood, in accordance with one embodiment of the present invention.

FIG. 9 is a block diagram of a cell extraction module 3000 for extracting cells from human blood. The extracted cells can then be used by system 100 (FIG. 2), system 700 and/or system 800 to manufacture a therapeutic protein using cells extracted from human blood. The extracted cells can be suitably housed in the fluid storage/dispensing module 400 in any of the systems 100/700/800.

The cell extraction module 3000 includes a whole blood separator 3100 and a blood cell lysing module 3200. The whole blood separator can be suitably implemented with the use of a simple collection tube (when left standing in a tube, the blood will separate by gravity) or with the use of a centrifuge to speed up the process. Generally, any known techniques for fractionating blood may be used by implemented by the whole blood separator 3100. The whole blood cell lysing module can be suitably implemented by using devices that apply mechanical, osmotic or high-pressure shock to the cells, electroporation, or use of lysing buffers or other methods for destroying the cell wall without affecting the proteins inside the cell. Generally, any known techniques for lysing the blood cells may be implemented by the whole blood cell lysing module 3200.

In operation, the whole blood separator receives whole blood 3150 and fractionates the blood. One or more blood cell fractions that will be used for manufacturing the therapeutic protein 3300 (e.g., erythrocytes, reticulocytes and/or lymphocytes) are collected sent to the blood cell lysing module 3200. It is important to collect cells that are highly metabolically active, as this will increase the productivity of the cell lysate. The separated plasma and unused fractions 3400 (i.e., red blood cells) are preferably stored to recombine with the therapeutic protein that is manufactured by the system 100/700/800 prior to injecting it into a patient. The return of the plasma and the red blood cells will obviate the need for blood transfusions, which may be required to replenish the withdrawn blood in the case where a large number of metabolically active cells needs to be harvested.

The blood cell lysing module 3200 utilizes a lysing reagent 3500, suitably an EDTA lysing reagent, to lyse the one or more blood fractions that will be used by system 100/700/800 to manufacture the therapeutic protein. The lysate 3600 produced by the blood cell lysing module 3200 is subjected to removal of the cells' nuclei and all other steps required in the production of a cell-free lysate, and then sent to system 100/700/800 for use in the manufacture of a therapeutic protein using the methods described above. The blood used to extract the cells needed for therapeutic protein manufacture is preferably obtained from the patient on which the manufactured protein will be used. In this way, all the leftover DNA and cellular proteins in the lysate are coming from the patient, which removes the possibility for immune reactions and greatly simplifies the purification procedures.

Figure 10:
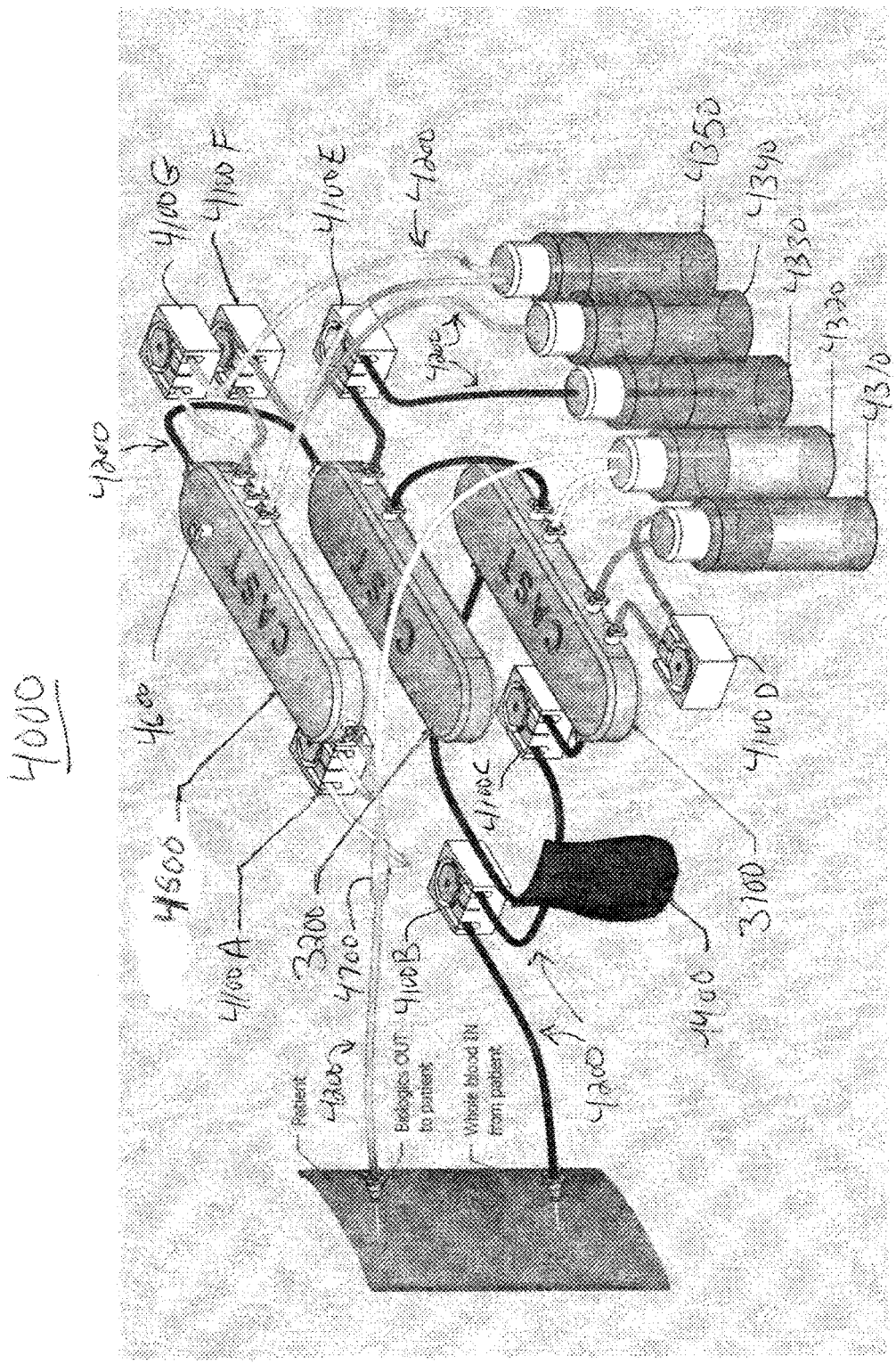
FIG. 10 is a schematic diagram of a bioprocessing system for manufacturing a therapeutic protein for a patient directly from a patient's own blood, in accordance with one embodiment of the present invention.

FIG. 10 is a schematic diagram of a bioprocessing system 4000 for manufacturing a therapeutic protein for a patient directly from a patient's own blood. Therapeutic protein production is accomplished by protein production module 4500 in a manner similar to systems 100, 700 and 800 above, except that the source of cell extracts for protein production comes from a patient's own blood using a whole blood separator 3100 and blood cell lysing module 3200, which are described above in connection with FIG. 9.

The system 4000 also includes a collection bag/reservoir 4400 for the blood, which acts as a holding container for the incoming whole blood, as well as a washing solution container 4310 for holding washing solution used by the whole blood separator 3100, a plasma container 4320 for holding plasma and unused blood fractions 3400 output by the whole blood separator 3100, an lysing reagent container 4330 for holding the lysing reagent used by the blood cell lysing module 3200, a reaction solution container 4340 for holding the reaction solution used by the protein production module 4500 and a buffer container 4350 for holding buffer solution used by the protein production module 4500. Protein production module 4500 also includes a DNA port 4600 for introduction of the DNA sequence that encode the therapeutic protein to be produced.

Multiple pumps 4100A-4100G and conduits 4200 are used to fluidly connect the various components of the system 4000 as shown in FIG. 10. In operation, whole blood from a patient is transported to the whole blood separator 3100, which fractionates the blood. The one or more blood fractions that will be used for protein production are sent to the blood cell lysing module 3200 to lyse the one or more blood fractions that will be used by the protein production module 4500 to manufacture the therapeutic protein. The lysing reagent used by the blood cell lysing module 3200 is suitably an EDTA lysing reagent that is drawn from the lysing agent container 4330. The plasma and unused blood fractions are stored in the plasma container 4320.

The therapeutic protein that is produced by the protein production module 4500 is mixed with the plasma and unused blood fractions stored in plasma container 4320 via coupler 4700, and then re-injected into the patient. Although the system 4000 is depicted and described as connected to a patient so as to draw whole blood directly from the patient and inject the patient with the therapeutic protein produced by the protein production module 4500 (mixed with plasma and unused fractions from plasma container 4320), it should be appreciated that the system 4000 does no have to be connected to the patient. Whole blood could be obtained from the patient and placed in a container, which is then sent to whole blood separator 3100 to start the process. Similarly, the therapeutic protein produced by the protein production module 4500 could be stored in a container prior to its use on the patient that provided the whole blood, or another patient.

In addition to pumps 4100A-4100G, any number of other hydraulic components, such as additional pumps, valves, couplers, etc. may be used throught the system 4000 to assist in controlling the flow of solution/product between the various components of the system 4000. The various pumps 4100A-4100G can suitably be implemented with an MP-6 pump (a piezoelectric pump, available from Bartels Mikrotechnik, Germany), an N-1000 pump (a syringe pump, available from New Era Pump Systems, NY, USA), however any type of suitable pump known in the art may be used. The conduits 4200 are suitably implemented with tubing made of Tygon or other suitable plastic material.

The foregoing embodiments and advantages are merely exemplary, and are not to be construed as limiting the present invention. The present teaching can be readily applied to other types of apparatuses. The description of the present invention is intended to be illustrative, and not to limit the scope of the claims. Many alternatives, modifications, and variations will be apparent to those skilled in the art. Various changes may be made without departing from the spirit and scope of the invention, as defined in the following claims.

What is claimed is:

1. A system for expressing and purifying a desired protein from blood, comprising:
   a whole blood separator adapted for receiving whole blood and outputting (i) at least one blood fraction comprising at least one of erythrocytes, reticulocytes and lymphocytes and (ii) a plasma and unused portion fraction;
   a blood cell lysing module adapted for receiving and lysing the at least one blood fraction from the whole blood separator and outputting a lysate;
   a bioreactor, adapted for producing the desired protein utilizing cell-free protein expression, for receiving the lysate from the blood cell lysing module and producing the desired protein from the lysate via protein expression utilizing cDNA or mRNA for the desired protein; and
   a purification module for receiving the desired protein from the bioreactor and purifying the desired protein.

2. The system of claim 1, wherein the bioreactor has a capacity of 20 ml or less.

3. The system of claim 1, further comprising a diafiltration component for receiving the purified desired protein from the purification module and for further purifying the desired protein.

4. The system of claim 3, wherein the diafiltration component comprises: a product section for receiving purified desired protein from the purification module; and a buffer section for receiving a buffer solution.

5. The system of claim 4, wherein the diafiltration component comprises:
   a first substrate;
   a second substrate; and
   a diafiltration membrane positioned between the first and second substrates.

6. The system of claim 5, wherein the diafiltration component further comprises
   a flow cell; and
   tubing positioned within the flow cell, wherein the diafiltration membrane comprises the tubing material.

7. The system of claim 1, wherein the desired protein comprises a therapeutic protein and wherein the whole blood originates from a patient to whom the therapeutic protein will be administered.

8. The system of claim 5, wherein the product section comprises a serpentine-shaped channel formed on the first substrate and the buffer section comprises a serpentine-shaped channel formed on the second substrate, wherein the first and second serpentine-shaped channels substantially correspond with each other.

9. The system of claim 1, wherein the blood cell lysing module comprises at least one lysing reagent comprising EDTA.

10. The system of claim 1, wherein the bioreactor further comprises a fluid storage/dispenser comprising at least one container selected from the group consisting of a holding container, a washing solution container, a lysing reagent container, a reaction solution container, and a buffer container.

11. The system of claim 1, wherein the purification module comprises one of membrane chromatography or column chromatography.

12. The system of claim 1, wherein the bioreactor further comprises at least one optical chemical sensor positioned inside the bioreactor.

13. The system of claim 1, further comprising a first heating and cooling element positioned inside the bioreactor for controlling a temperature solution inside the bioreactor.

14. The system of claim 1, wherein the system further comprises a processor for controlling and/or monitoring the bioreactor and the purification module.

15. The system of claim 1, wherein the bioreactor further comprises a DNA port.

16. The system of claim 1, wherein the lysate is cell-free.

17. The system of claim 1, wherein the system further comprises a plasma and unused portion container in fluid communication with both the whole blood separator and a coupling unit, wherein the plasma and unused portion fraction is temporarily stored in the plasma and unused portion container.

18. The system of claim 17, wherein the coupling unit is in fluid communication with either the purification module or, when present, a diafiltration component, for combining the purified desired protein with the plasma and unused portion fraction.

19. The system of claim 1, wherein the blood cell lysing module comprises at least one of a mechanical lysis device, an osmotic shock lysis device, a high pressure shock lysis device or an electroporation lysis device.

* * * * *